(12) United States Patent
Stowe et al.

(10) Patent No.: US 9,592,699 B2
(45) Date of Patent: *Mar. 14, 2017

(54) DAMPENING FLUID FOR DIGITAL LITHOGRAPHIC PRINTING

(75) Inventors: Timothy D. Stowe, Alameda, CA (US); Eric Peeters, Fremont, CA (US); Chu-Heng Liu, Penfield, NY (US)

(73) Assignees: Xerox Corporation, Norwalk, CT (US); Palo Alto Research Center Incorporated, Palo Alto, CA (US)

(*) Notice: Subject to any disclaimer, the term of this patent is extended or adjusted under 35 U.S.C. 154(b) by 1375 days.

This patent is subject to a terminal disclaimer.

(21) Appl. No.: 13/284,114

(22) Filed: Oct. 28, 2011

(65) Prior Publication Data
US 2013/0104756 A1    May 2, 2013

(51) Int. Cl.
B41N 3/08    (2006.01)
B41M 1/06    (2006.01)

(52) U.S. Cl.
CPC .............. B41N 3/08 (2013.01); B41M 1/06 (2013.01)

(58) Field of Classification Search
CPC ........................................................ B41N 3/08
See application file for complete search history.

(56) References Cited

U.S. PATENT DOCUMENTS 8,919,252 B2 * 12/2014 Lestrange et al. ............ 101/478
2002/0121206 A1 * 9/2002 Ooishi .................. B41C 1/1041
101/450.1
2008/0299487 A1    12/2008 Chang
2012/0103212 A1 *  5/2012 Stowe .................. B41C 1/1041
101/147
2012/0274914 A1 * 11/2012 Stowe ...................... B41F 7/00
355/53

FOREIGN PATENT DOCUMENTS

EP    2 447 065 A1    5/2012
EP    2 450 190 A1    5/2012

OTHER PUBLICATIONS

Examination Report in corresponding European Patent Application No. 12190034.4 dated Jan. 3, 2014.
Amended European Search Report in corresponding European Patent Application No. 12190034.4 dated Oct. 22, 2013.
Partial European Search Report in corresponding European Patent Application No. 12190034.4 dated Jan. 15, 2013.
Anthony J. O'Lenick, Jr., "Silicones for Personal Care, 2nd Edition," Chapter 2, pp. 35-41, "Basic Silicone Materials," published 2008, ISBN-10: 1-932633-36-7.
Yonezo Kato, Frederick M. Fowkes, and John W. Vanderhoff, "Surface Energetics of the Lithographic Printing Process," Ind. Eng. Chem. Prod. Res. Dev. 1982, vol. 21, pp. 441-450, 1982 American Chemical Society.

* cited by examiner

Primary Examiner — Joshua D Zimmerman
(74) Attorney, Agent, or Firm — Prass LLP

(57) ABSTRACT

Different solvents for a dampening fluid are disclosed. The solvent is a volatile hydrofluoroether liquid or a volatile silicone liquid. Such liquids have a lower heat of vaporization, a lower surface tension, and better kinematic viscosity compared to water, which is the conventional solvent used in dampening fluids. The dampening fluids, which are relatively nonpolar, can be used in a combination with polar inks to form a new type of digital lithographic printing system.

1 Claim, 5 Drawing Sheets

DAMPENING FLUID FOR DIGITAL LITHOGRAPHIC PRINTING

CROSS-REFERENCE TO RELATED APPLICATIONS

The present disclosure is related to U.S. patent application Ser. No. 13/095,714, filed on Apr. 27, 2011, titled "Variable Data Lithography System", the entirety of which is incorporated herein by reference.

BACKGROUND

The present disclosure relates to the use of certain solvents in dampening fluids used during variable data lithographic printing. This disclosure also relates to apparatuses using such dampening fluids, and methods of using such dampening fluids, such as in variable lithographic printing applications.

Offset lithography is a common method of printing today. (For the purposes hereof, the terms "printing" and "marking" are interchangeable.) In a typical lithographic process a printing plate, which may be a flat plate, the surface of a cylinder, or belt, etc., is formed to have "image regions" formed of a hydrophobic/oleophilic material, and "non-image regions" formed of a hydrophilic/oleophobic material. The image regions correspond to the areas on the final print (i.e., the target substrate) that are occupied by a printing or marking material such as ink, whereas the non-image regions correspond to the areas on the final print that are not occupied by said marking material. The hydrophilic regions accept and are readily wetted by a water-based fluid, commonly referred to as a dampening fluid or fountain fluid (typically consisting of water and a small amount of alcohol as well as other additives and/or surfactants to reduce surface tension). The hydrophobic regions repel dampening fluid and accept ink, whereas the dampening fluid formed over the hydrophilic regions forms a fluid "release layer" for rejecting ink. The hydrophilic regions of the printing plate thus correspond to unprinted areas, or "non-image areas", of the final print.

The ink may be transferred directly to a target substrate, such as paper, or may be applied to an intermediate surface, such as an offset (or blanket) cylinder in an offset printing system. The offset cylinder is covered with a conformable coating or sleeve with a surface that can conform to the texture of the target substrate, which may have surface peak-to-valley depth somewhat greater than the surface peak-to-valley depth of the imaging plate. Also, the surface roughness of the offset blanket cylinder helps to deliver a more uniform layer of printing material to the target substrate free of defects such as mottle. Sufficient pressure is used to transfer the image from the offset cylinder to the target substrate. Pinching the target substrate between the offset cylinder and an impression cylinder provides this pressure.

Typical lithographic and offset printing techniques utilize plates which are permanently patterned, and are therefore useful only when printing a large number of copies of the same image (i.e. long print runs), such as magazines, newspapers, and the like. However, they do not permit creating and printing a new pattern from one page to the next without removing and replacing the print cylinder and/or the imaging plate (i.e., the technique cannot accommodate true high speed variable data printing wherein the image changes from impression to impression, for example, as in the case of digital printing systems). Furthermore, the cost of the permanently patterned imaging plates or cylinders is amortized over the number of copies. The cost per printed copy is therefore higher for shorter print runs of the same image than for longer print runs of the same image, as opposed to prints from digital printing systems.

Accordingly, a lithographic technique, referred to as variable data lithography, has been developed which uses a non-patterned reimageable surface that is initially uniformly coated with a dampening fluid layer. Regions of the dampening fluid are removed by exposure to a focused radiation source (e.g., a laser light source) to form pockets. A temporary pattern in the dampening fluid is thereby formed over the non-patterned reimageable surface. Ink applied thereover is retained in the pockets formed by the removal of the dampening fluid. The inked surface is then brought into contact with a substrate, and the ink transfers from the pockets in the dampening fluid layer to the substrate. The dampening fluid may then be removed, a new uniform layer of dampening fluid applied to the reimageable surface, and the process repeated.

The patterning of dampening fluid on the reimageable surface member in variable data lithography essentially involves using a laser or some other energy source to selectively boil off or ablate the dampening fluid in selected locations. This process can be energy intensive due to the large latent heat of vaporization of water. At the same time, high-speed printing necessitates the use of high-speed modulation of that energy source, which can be prohibitively expensive for high power lasers. Therefore, from both an energy and cost perspective, it would beneficial to reduce the total amount of energy that is needed to achieve pattern-wise vaporization of the dampening fluid.

The essential role of the dampening fluid in both traditional offset printing and in variable lithographic printing is to provide selectivity for the imaging and transfer of the ink. Dampening fluid generally contains water and some additives to reduce surface tension, such as a surfactant. The dampening fluid acts as a low viscosity release layer film which preferentially splits at the inking nip, thus preventing ink adhesion to the imaging member surface. In addition, the dampening fluid is to a large degree immiscible with the ink chemistry, being oleophobic in its chemical nature. Otherwise, the dampening fluid can break apart into small emulsified droplets with the ink which can lead to background tinting.

As already discussed above, an additional consideration in variable lithographic printing is the energy necessary to boil off the dampening fluid. For example, water is a very polar molecule and has both high surface tension and a high latent heat of vaporization, which relates to the energy required to change water from its liquid phase to its vapor phase. The high heat of vaporization leads to high energy requirements for the laser used to vaporize the dampening fluid.

A further consideration related to the thermal properties of the dampening fluid is the dampening fluid boiling temperature. Too low a boiling temperature will mean quick thinning of the fluid due to its partial pressure evaporation near room temperature. It is desirable to have a high enough boiling temperature such that the evaporation rate does not compete with the laser boiling process because this insures better image definition. On the other hand, too high a boiling temperature means added laser energy is necessary due to the specific heat of the dampening fluid required for raising its temperature up to the boiling point, and this can therefore reduce the overall printing speed for a given laser power. The high surface tension of water causes the dampening fluid to tend to bead, rather than to spread evenly over the surface of the imaging member. To reduce the surface tension, dampening fluid usually includes another solvent which is less polar than water, such as isopropanol (IPA). However, isopropanol is a volatile organic compound (VOC), and its emission is regulated. In addition variable lithographic imaging typically uses an elastomeric surface, and IPA is known to cause swelling in may many elastomeric surface materials. Other aqueous-based surfactants tend to have high boiling points and therefore leave a residue behind on the surface of the imaging member, compromising the integrity of the imaging member for making images of suitable quality.

It would be desirable to provide dampening fluids that can avoid such problems for variable lithographic printing.

BRIEF DESCRIPTION

Disclosed in various embodiments are dampening fluids, systems, and processes that are useful for variable lithographic printing. Conventional offset lithographic systems use a polar dampening fluid and a non-polar ink to form the images. In the present disclosure, the dampening fluid is relatively non-polar and the ink is relatively polar instead. By choosing the proper reimageable imaging member chemistry, ink chemistry, and dampening fluid chemistry, a system can be arrived at wherein both the ink and the dampening fluid will wet the surface of the rewriteable imaging member, and the dampening fluid will still energetically maintain its wetting of the surface in the presence of the ink. Such a configuration is arrived at by considering the wetting conditions over a surface with regards to both the polar and dispersive components of the surface tensions and energies of all three components: imaging member surface, ink, and dampening fluid. Among other advantages, this system actually allows the dampening fluid to clean off any small ink residues left behind by previous passes of the imaging member when a new layer of dampening solution is applied after each print pass.

Disclosed in embodiments is a dampening fluid for variable lithographic printing. The dampening fluid comprises a solvent which is a volatile hydrofluoroether liquid or a volatile silicone liquid. These classes of fluids provides advantages in the amount of energy needed to evaporate, desirable characteristics in the dispersive/polar surface tension design space, and the additional benefit of zero residue left behind once evaporated.

The solvent may be a volatile hydrofluoroether liquid having the structure of Formula (I):

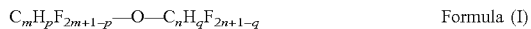

$$C_mH_pF_{2m+1-p}-O-C_nH_qF_{2n+1-q}$$ Formula (I)

wherein m and n are independently integers from 1 to about 9; and p and q are independently integers from 0 to 19.

In particular embodiments, q is zero and p is non-zero. Exemplary volatile hydrofluoroether liquids include those having the structure of any one of Formulas (I-a) through (I-h):

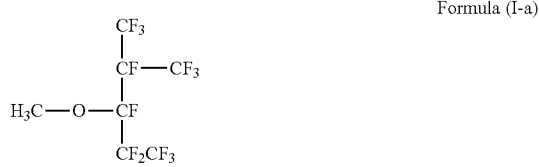

(Formula I-a)

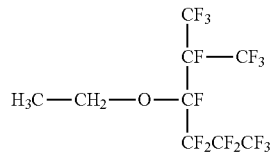

(Formula I-b)

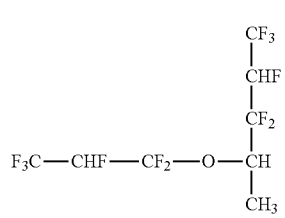

Formula (I-c)

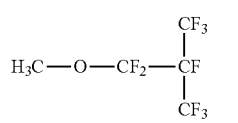

(Formula I-d)

H₃C—O—CF₂CF₂CF₂CF₃  Formula (I-e)

H₃C—O—CF₂CF₂CF₃  (Formula I-f)

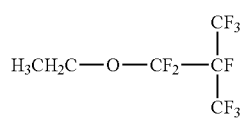

Formula (I-g)

H₃CH₂C—O—CF₂CF₂CF₂CF₃.  Formula (I-h)

The solvent may be a volatile silicone liquid having the structure of Formula (II):

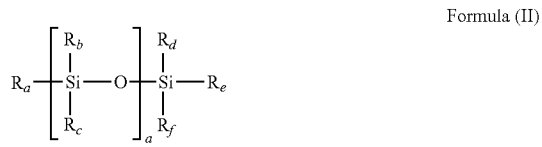

Formula (II)

wherein $R_a$, $R_b$, $R_c$, $R_d$, $R_e$, and $R_f$ are each independently hydrogen, alkyl, or perfluoroalkyl; and a is an integer from 1 to about 5. In particular embodiments, the volatile silicone liquid is hexamethyldisiloxane or octamethyltrisiloxane.

The volatile silicone liquid may alternatively have the structure of Formula (III):

Formula (III)

wherein each $R_g$ and $R_h$ is independently hydrogen, alkyl, or perfluoroalkyl; and b is an integer from 3 to about 8.

The volatile silicone liquid can be octamethylcyclotetrasiloxane or decamethylcyclopentasiloxane. In specific embodiments, the volatile silicone liquid is a mixture of octamethylcyclotetrasiloxane and decamethylcyclopentasiloxane.

The volatile silicone liquid can also be a mixture of hexamethylcyclotrisiloxane and octamethylcyclotetrasiloxane. Hexamethylcyclotrisiloxane (aka D3) usually forms a solid at room temperature but when a small amount is added to octamethylcyclotetrasilonxane, typically less than 30% by total weight, the mixture will form a continuous fluid. The advantage of this mixture is the boiling temperature of octamethylcyclotretrasiloxane can be reduced thereby reducing the laser power needed.

The volatile silicone liquid may also have the structure of Formula (IV):

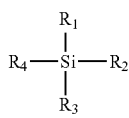

Formula (IV)

wherein $R_1$, $R_2$, $R_3$, and $R_4$ are independently alkyl or $-OSiR_1R_2R_3$.

The volatile silicone liquid may have the structure of Formula (IV-a):

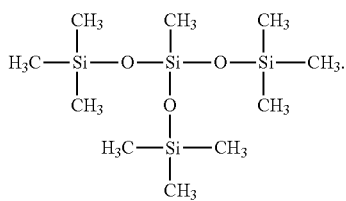

Formula (IV-a)

The dampening fluid may have a surface tension of from about 15 to about 30 dynes/cm. In particular embodiments, the dampening fluid has a kinematic viscosity greater than 1 centiStokes at 25° C. and a surface tension of less than 72 dynes/cm at 25° C. In other embodiments, the solvent has a heat of vaporization of less than 120 kJ/kg when measured at 1 atmosphere and 25° C.

Also disclosed is a process for variable lithographic printing using such dampening fluids disclosed. A dampening fluid is applied to an imaging member surface, wherein the dampening fluid comprises a solvent which is a volatile hydrofluoroether liquid or a volatile silicone liquid. A latent image is formed by evaporating the dampening fluid from selective locations on the imaging member surface to form hydrophobic non-image areas and hydrophilic image areas. The latent image is developed by applying a polar ink to the hydrophilic image areas. The developed latent image is then transferred to a receiving substrate.

The polar ink may comprise an acrylate monomer. Alternatively, the polar ink may comprise a monomer containing an ester, ether, carbonyl, amino, cyano, or hydroxyl group. In other embodiments, the polar component of the surface tension of the ink is larger than the polar component of the surface tension of the dampening fluid.

Also disclosed in embodiments is a dampening fluid for variable lithographic printing, which comprises a solvent having a heat of vaporization of less than 200 kJ/kg.

Also disclosed in various embodiments is a variable lithographic system comprising an ink, a dampening fluid, and an imaging member surface. The dampening fluid has a surface energy which is less than the surface energy of the ink and the surface energy of the imaging member surface. In embodiments, the dampening fluid has a total surface energy of less than 30 dynes/cm and a polar surface energy component less than 5 dyne/cm. The imaging member surface may have a surface energy of less than 30 dynes/cm.

These and other non-limiting aspects and/or objects of the disclosure are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
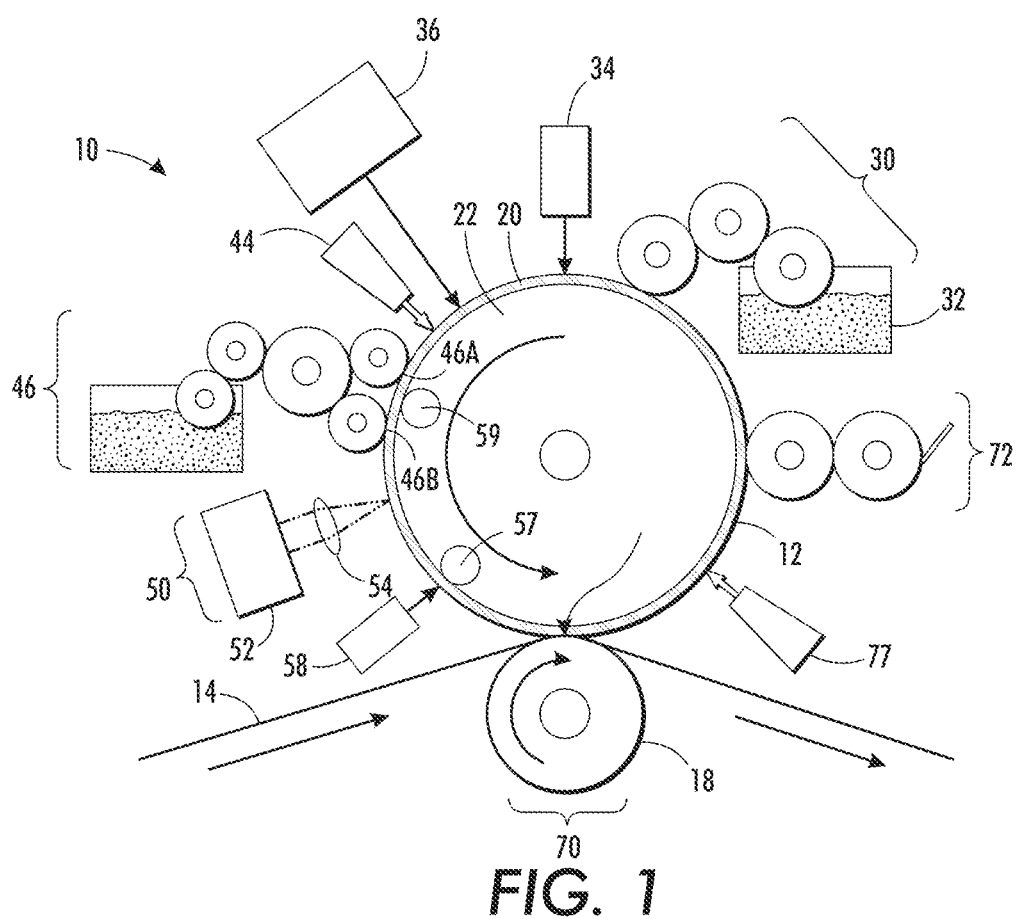
FIG. 1 illustrates a variable lithographic printing apparatus in which the dampening fluids of the present disclosure may be used.

A more complete understanding of the processes and apparatuses disclosed herein can be obtained by reference to the accompanying drawings. These figures are merely schematic representations based on convenience and the ease of demonstrating the existing art and/or the present development, and are, therefore, not intended to indicate relative size and dimensions of the assemblies or components thereof.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The modifier "about" used in connection with a quantity is inclusive of the stated value and has the meaning dictated by the context (for example, it includes at least the degree of error associated with the measurement of the particular quantity). When used with a specific value, it should also be considered as disclosing that value. For example, the term "about 2" also discloses the value "2" and the range "from about 2 to about 4" also discloses the range "from 2 to 4."

FIG. 1 illustrates a system for variable lithography in which the dampening fluids of the present disclosure may be used. The system 10 comprises an imaging member 12. The imaging member comprises a substrate 22 and a reimageable surface layer 20. The surface layer is the outermost layer of the imaging member, i.e. the layer of the imaging member furthest from the substrate. As shown here, the substrate 22 is in the shape of a cylinder; however, the substrate may also be in a belt form, etc. The surface layer 20 is typically a silicone (e.g. a methylsilicone or fluorosilicone), which may have carbon black added to increase energy absorption of the surface layer.

In the depicted embodiment the imaging member 12 rotates counterclockwise and starts with a clean surface. Disposed at a first location is a dampening fluid subsystem 30, which uniformly wets the surface with dampening fluid 32 to form a layer having a uniform and controlled thickness. Ideally the dampening fluid layer is between about 0.15 micrometers and about 1.0 micrometers in thickness, is uniform, and is without pinholes. As explained further below, the composition of the dampening fluid aids in leveling and layer thickness uniformity. A sensor 34, such as an in-situ non-contact laser gloss sensor or laser contrast sensor, is used to confirm the uniformity of the layer. Such a sensor can be used to automate the dampening fluid subsystem 30.

At optical patterning subsystem 36, the dampening fluid layer is exposed to an energy source (e.g. a laser) that selectively applies energy to portions of the layer to imagewise evaporate the dampening fluid and create a latent "negative" of the ink image that is desired to be printed on the receiving substrate. Image areas are created where ink is desired, and non-image areas are created where the dampening fluid remains. An optional air knife 44 is also shown here to control airflow over the surface layer 20 for the purpose of maintaining clean dry air supply, a controlled air temperature, and reducing dust contamination prior to inking. Next, an ink is applied to the imaging member using inker subsystem 46. Inker subsystem 46 may consist of a "keyless" system using an anilox roller to meter an offset ink onto one or more forming rollers 46A, 46B. Ink is applied to the image areas to form an ink image.

A rheology control subsystem 50 partially cures or tacks the ink image. This curing source may be, for example, an ultraviolet light emitting diode (UV-LED) 52, which can be focused as desired using optics 54. Another way of increasing the cohesion and viscosity employs cooling of the ink. This could be done, for example, by blowing cool air over the reimageable surface from jet 58 after the ink has been applied but before the ink is transferred to the final substrate. Alternatively, a heating element 59 could be used near the inker subsystem 46 to maintain a first temperature and a cooling element 57 could be used to maintain a cooler second temperature near the nip 16.

The ink image is then transferred to the target or receiving substrate 14 at transfer subsystem 70. This is accomplished by passing a recording medium or receiving substrate 14, such as paper, through the nip 16 between the impression roller 18 and the imaging member 12.

Finally, the imaging member should be cleaned of any residual ink or dampening fluid. Any dampening solution residue can be easily removed quickly using an air knife 77 with sufficient air flow. Removal of any remaining ink can be accomplished at cleaning subsystem 72.

The role of the dampening fluid is to provide selectivity in the imaging and transfer of ink to the receiving substrate. When an ink donor roll in the ink source of FIG. 1 contacts the dampening fluid layer, the layer splits so that ink is only applied to areas on the imaging member that are dry, i.e. not covered with dampening fluid.

As discussed above, water is usually the majority component of the dampening fluid (by weight). Water itself has a high latent heat of vaporization, which leads to high energy requirements at the imaging station.

In addition, water has a high surface tension of around 70 dynes/cm. This reduces the ability of the dampening fluid to quickly form a thin film on the imaging member surface. One conventional solvent that is sometimes also added to reduce surface tension is isopropyl alcohol (i.e. isopropanol). However, isopropanol is a volatile organic compound (VOC), and environmental regulations typically require lower emissions. For example, the state of California requires that the amount of isopropanol either be less than 5%, or that printing production equipment have solvent reclaim systems to capture the emissions. At this level of isopropanol, the surface tension is still too high to give good performance.

Thus, to reduce surface tension further, surfactants are typically added to the water to lower the surface tension to around 20-30 dynes/cm. However, such surfactants usually consist of copolymer molecules with hydrophilic heads and hydrophobic tails which must be long enough to adequately wet both the surface of the imaging member and the dampening fluid, and these copolymer molecules tend to have high boiling points above 200° C. As a result, these copolymer molecules can plate out non-uniformly as a residue when the water is evaporated, leading to variability in the printing process as well as dampening fluid layer ghosting, which occurs when the residue on the surface slightly affects the thickness of a new layer of dampening fluid that is subsequently laid down. A dampening fluid that produces little or no residual surfactant residue is needed to provide precision control over the thickness of the dampening fluid.

In addition, water has a low kinematic viscosity of about 1 centiStoke (1 mm$^2$/sec). Generally, the dampening fluid must have a positive spreading coefficient so that it can adequately wet the surface of the imaging member when initially laid down. However, during the imaging process where dampening fluid is heated and evaporated to form the latent image, the adjacent dampening fluid is also partially heated. This partial heating further lowers the kinematic viscosity of the adjacent dampening fluid, allowing it to either spread or pull back, depending on the geometry of the latent image formed. For sharp convex corners in letters such as "W" or "V", a pull-back effect occurs that leads to a rounding of concave corners in the ink when printing. For lines without curvature, the dampening fluid exhibits a tendency to spread and fill in evaporated areas, especially for thicker layers of dampening fluid (~2 μm thickness). Over millisecond time scales, water-based dampening fluid will spread somewhat even when the surface of the imaging member has a proper level of surface roughness to help pin the dampening fluid in place. Sometimes arabic gum is added to dampening fluid to increase the viscosity. However, arabic gum also has a high boiling point and can leave residue behind.

It should be noted that one advantage of a water-based dampening fluid is that water has a high polar component to its surface tension (surface tension can be separated into two components, a polar component and a dispersive component). This helps the dampening fluid reject ink, which tends to have a low polar surface tension and high dispersive surface tension. As a result, the interfacial surface energy between the ink and the dampening fluid remains high, and they mutually do not wet one another.

As a result, a desirable solvent for a dampening fluid should be a liquid having a low heat of vaporization, low surface tension, and high kinematic viscosity. Unfortunately, liquids having these three components tend to have a high dispersive surface tension component and a low polar surface tension component. In a conventional lithographic printing system, these liquids would tend to mix more readily with a polymer/oil-based ink, which also tends to have high dispersive surface tension and low polar surface tension. This would lead to background effects in the non-imaging areas (where ink is not applied) and tinting in the imaging areas.

It should be noted that silicones or fluorosilicones are considered desirable and useful materials for the surfaces of an imaging member because they have low surface free energy and excellent ink release properties under a pressurized nip. Such materials typically have a siloxane backbone with methyl (—$CH_3$) or trifluoromethyl (—$CF_3$) side chains. However, it is well known that many liquids cause elastomeric materials to swell. It would be preferable to use a liquid for the dampening fluid solvent that does not act as a plasticizer or solvent to these rubbery materials to provide for long surface lifetime without wear. Some solvents have such a low molecular weight that they inevitably cause some swelling of silicones and fluorosilicones depending upon the degree of fluoro substitution. Wear can proceed indirectly under these swell conditions by causing the release of near infrared laser energy-absorbing particles at the imaging member surface, such as carbon black. These particles then act as abrasive particles. Desirably, the dampening fluid liquid/solvent should have a low tendency for swell or elastomer penetration.

If possible, it would be desirable for the dampening fluid to be easily recyclable. This is useful both in reducing total waste and in lowering the overall cost of the system. It would be helpful if the dampening fluid liquid had a density that was very different compared to water, so that the liquid can be more easily separated if recondensed. The liquid is also desirably non-toxic, exempt from VOC regulations, have a low global warming potential, have low to no ozone depletion potential, and easily handled/transported.

In conventional offset printing systems, the dampening fluid is primarily composed of water. The dampening fluid and ink have a polar and dispersive relationship designed to wet the non-imaging and imaging areas of the static offset plate respectively. Often surface energy models are used to describe the interactive surface energies between an imaging surface, the ink, and the dampening fluid. These surface energy models are useful in predicting the wettability of one fluid in the presence of another over an idealized surface and are described in detail in many prior art references. One such review article is written by Yonezo Kato, Frederick M. Fowkes, and John W. Vanderhoff entitled "Surface energetics of the lithographic printing process", *Ind. Eng. Chem. Prod. Res. Dev.*, 1982, 21 (3), pp 441-450.

According to such surface energy models, the surface tension of any fluid or the surface energy of an imaging surface can be represented in air as being primarily composed of dispersive and polar components according to the relationship of equation (i):

$$\gamma = \gamma_d + \gamma_p = \alpha^2 + \beta^2 \quad (i)$$

where $\gamma$ is the total surface energy (or surface tension for a liquid) in units of $J/m^2$ or more commonly given in dynes/cm. The total surface energy is composed of two orthogonal components, the dispersive component $\gamma_d$ and polar component $\gamma_p$, which act to a large degree independently. The polar and dispersive components of surface tension for a liquid or surface energy for a solid can be calculated from tensionmeter or contact angle measurements known in the art using commercial scientific equipment provided by several equipment companies including, for example, First Ten Angstroms, Inc located in Portsmouth, Va., Diversified Enterprises located in Claremont, N.H., or Biolin Scientific Inc. located in Linthicum Heights, Md. Alpha and beta of equation (i) are further defined according to equations (ii) and (iii):

$$\alpha = \sqrt{\gamma_d} \quad (ii)$$

$$\beta = \sqrt{\gamma_p} \quad (iii)$$

Alpha and beta are useful in describing molecular surface interactions acting across molecular distances. Hydrogen bonding components of the liquid surface tensions are usually not included in these models because they give rise to small effects but it should be noted they cannot be neglected in determining the chemical compatibility and miscibility of the dampening solution and ink chemistries, i.e. the diffusion of one fluid into another.

The total surface energy $\gamma$ of equation (i) applies to surfaces as measured in vacuum or in dry air. However, the measured values for surface tension often change when two fluids or a fluid and solid surface come in contact. Generally, the surface tension that develops between any two constituents a and b (in the absence of air) is often referred to as $\gamma_{ab}$. Thus, the surface tension between ink (i) and dampening fluid (f) is often denoted as $\gamma_{if}$. Similarly, the surface tension between ink (i) and the imaging surface (s) is often written as $\gamma_{is}$.

It has been found both empirically and theoretically that this interaction energy can be estimated to a good degree by the Fowke's model for the interaction energy of equation (iv):

$$\gamma_{ab} \approx \gamma_a + \gamma_b - 2\alpha_a\alpha_b - 2\beta_a\beta_b \quad (iv)$$

From these simple models, various spreading coefficients can be calculated from an understanding of Young's equation which describes the equilibrium behavior of a fluid over a surface and dynamic interactions associated with the spreading. The condition for the dampening fluid (f) to energetically spread uniformly over an imaging plate (s) in a non-image area is given by a positive spreading coefficient $S_f > 0$ of the dampening fluid over the imaging surface in the presence of air, as shown in equation (v):

$$S_f = r\gamma_s - \gamma_f - r\gamma_{fs} \quad (v)$$

where the term r is an enhancement factor if the surface has microroughness or microtexture which tends to increase the effective interfacial energy provide air is not trapped within the texture.

Similarly, the condition for the ink (i) to uniformly wet the imaging plate (s) in an image area is given by a positive ink spreading coefficient $S_i > 0$ of the ink over the imaging surface in the presence of air, as shown in equation (vi):

$$S_i = r\gamma_s - \gamma_i - r\gamma_{is} \quad (vi)$$

The condition for the dampening fluid (f) to reliably wet the imaging plate (i) in the non-image area and reject ink (i) in the non-image area (when an ink roller is presented over a layer of dampening fluid) is given by a positive spreading coefficient of the dampening fluid in the presence of ink $S_{fi} > 0$ as shown in equation (vii):

$$S_{fi} = r\gamma_{is} - \gamma_{fi} - r\gamma_{fs} \quad (vii)$$

Figure 2:
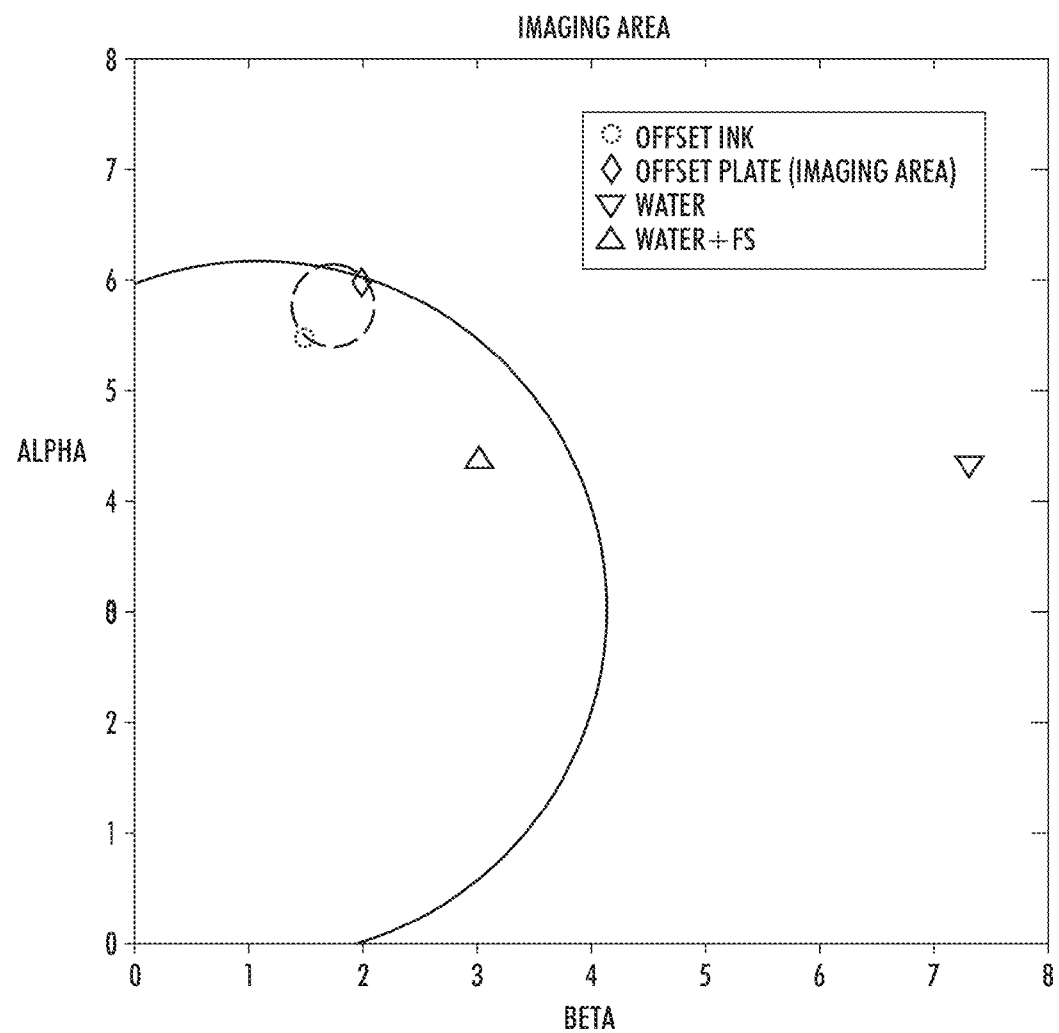
FIG. 2 is an alpha versus beta graph depicting the wetting conditions in the image area of an offset plate for a conventional oil-based offset ink.
Figure 3:
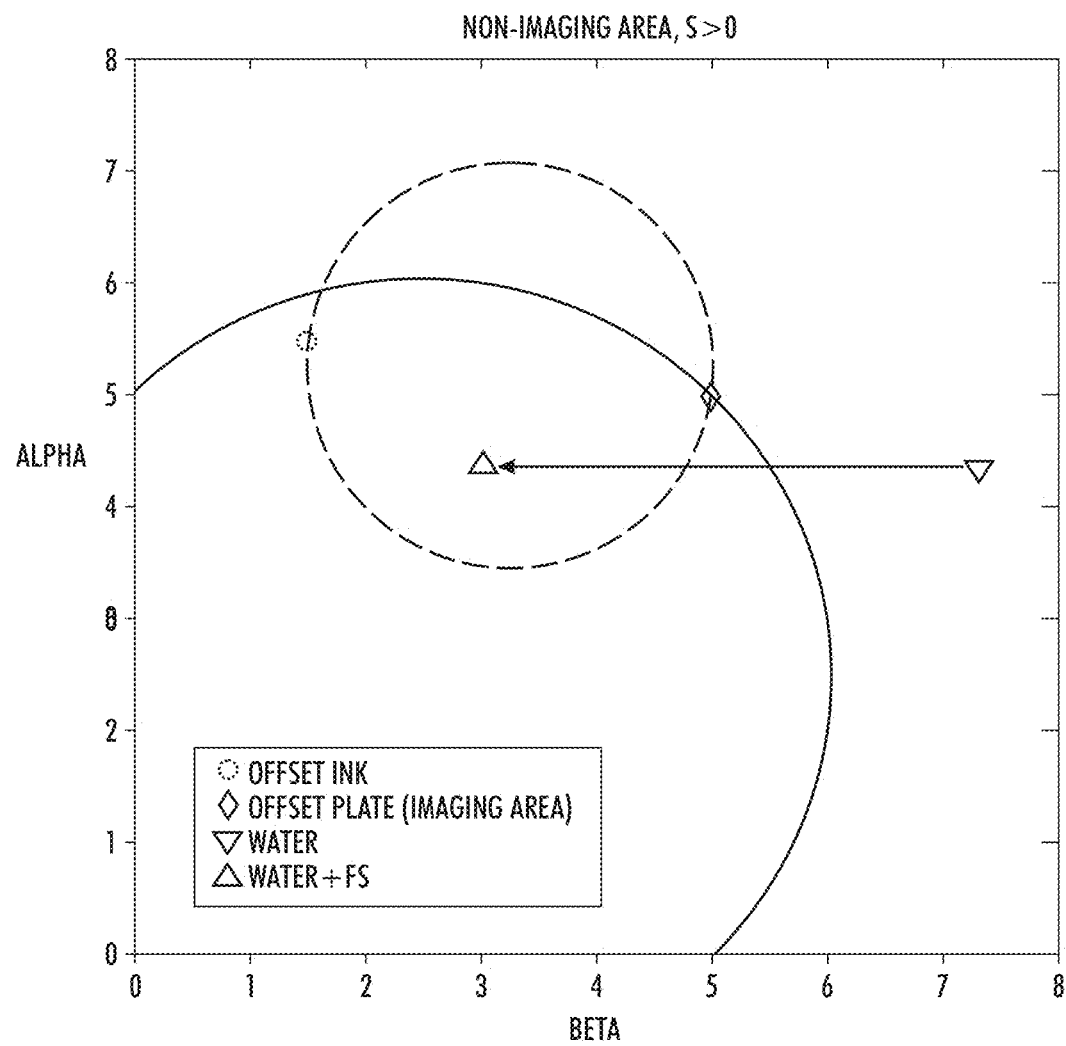
FIG. 3 is an alpha versus beta graph depicting the wetting conditions of a conventional water-based offset dampening fluid in the non-image area of an offset plate. The dotted circle represents the wetting condition of the dampening fluid in the presence of ink.
Figure 4:
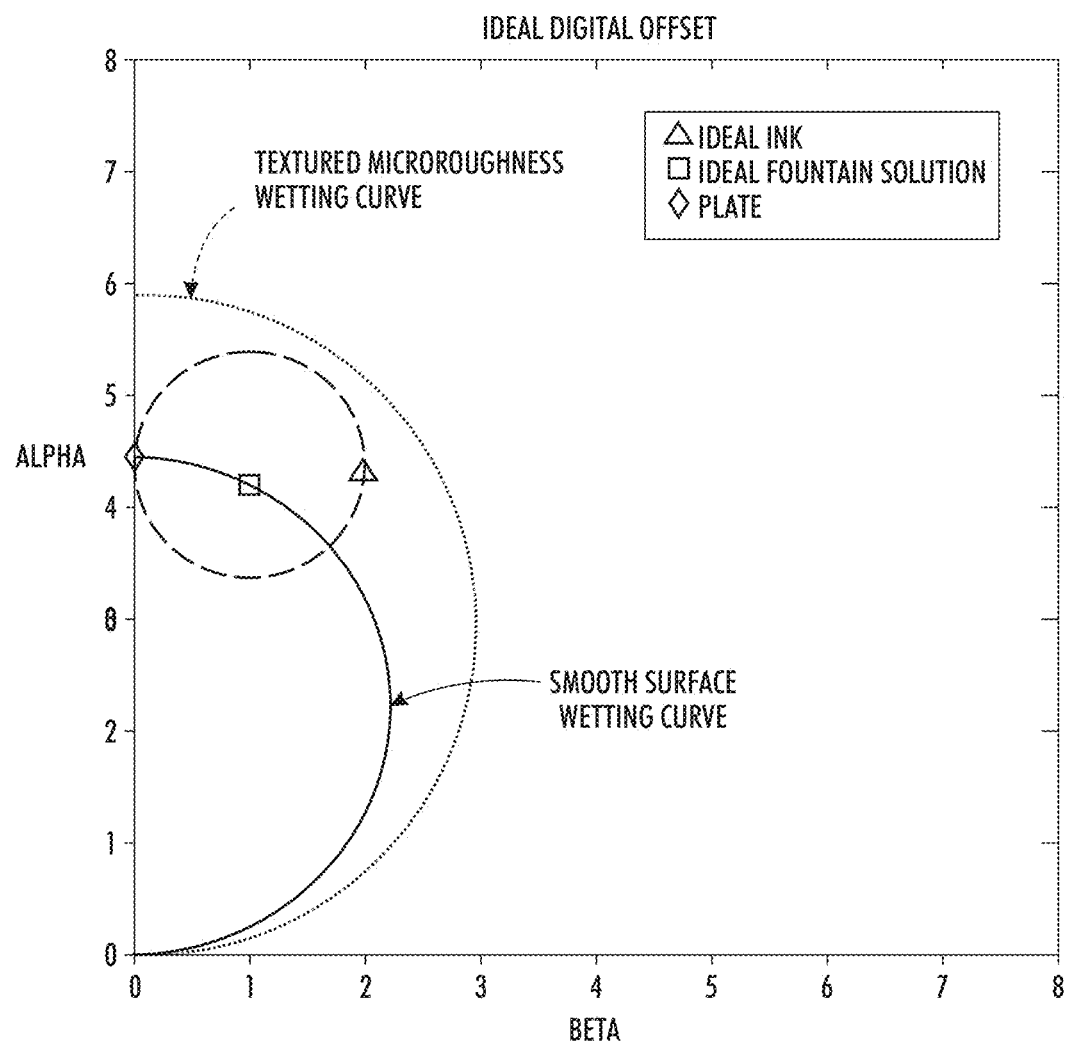
FIG. 4 is an alpha versus beta graph depicting the wetting conditions obtained for variable lithographic printing in the present disclosure, wherein both ink and dampening fluid can both wet the surface of the imaging member simultaneously and the dampening fluid also wets the plate in the presence of ink (seen as the dotted circle).

Often the surface energies of the ink, dampening fluid, and printing surface are plotted on a graph of alpha (y-axis) versus beta parameters (x-axis), which is useful in illustrating the wetting phenomenon. Referring now to FIGS. 2-4, on such graphs the solution for each component wherein the spreading coefficient S is equal to zero is graphically represented by a circle also known as the wetting envelope. For the spreading coefficient of a liquid over a surface in the presence of air, these circles have their center at the origin. When one considers the spreading coefficient of a fluid in the presence of another fluid besides air, such wetting envelopes no longer have their centers at the origin. Fluids having alpha-beta surface tension parameters that lie inside these circles typically wet a surface and have a positive spreading coefficient, whereas fluids having alpha-beta parameters outside these circles typically do not spread over the surface, but form droplets with a wetting contact angle given by Young's equation.

It is necessary, but not sufficient, that all three of these spreading conditions described by the conditions (v, vi, and vii) above be satisfied in the imaging system in order to achieve good print quality. In the past, these three spreading conditions have been satisfied in traditional offset printing by patterning the imaging plate to have two separate regions, an imaging region with surface energy $\gamma_{s1}$ and a non-imaging region with surface energy $\gamma_{s2}$. These regions preferentially accept either the dampening fluid or the ink, but not both. In other words, the plate is composed of hydrophilic/oleophobic non-image areas and hydrophobic/oleophilic image areas which have mutually exclusive wetting characteristics such that different surface energies applies for simultaneously solving equations (v), (vi), and (vii). These conditions can be graphically plotted in two separate alpha beta plots as shown in FIG. 2 and FIG. 3, which correspond to imaging and non-imaging areas of the plate. For these plots we have assumed r~1, but the interpretation of these plots do not change if r assumes higher values.

Referring to FIG. 2, the solid line circle represents an enclosed alpha-beta region of solutions which will wet the imaging area on a plate. The position of the diamond on the circle corresponds to the surface energy of the imaging area on the plate, i.e. the alpha-beta coordinates of the plate's surface energy. Similarly, the ink surface tension is represented by the dotted circle and is inside the offset plate's circle, indicating that the ink will wet the surface of the offset plate. The inverted triangle (beta~7, alpha~4) represents water, and indicates that water alone will not wet the surface of the offset plate, due to its high surface tension. However, when a surfactant is added to the water to form a fountain solution (FS), the effective beta component (i.e. polarity) decreases dramatically resulting in a new position on the alpha beta plot (beta~3, alpha~4) within the surface wetting circle. This new position is represented by the upright triangle. The dashed circle connecting the diamond and the dotted circle represents the wetting envelope where wetting will occur on imaging areas of the surface in the presence of ink (condition vii, when $S_{fi}$=0). The fact that the fountain solution is outside the dashed circle indicates that the surface of the imaging area is preferentially wetted by the ink.

FIG. 3, in contrast, presents the situation over the non-imaging areas of a plate. Here the plate surface energy has a much higher polar component and therefore the wetting circle indicated by the solid line circle is much larger. This time, the fountain solution surface tension (represented by dotted circle) falls within both the solid line circle wetting envelope and within the dashed circle wetting envelope. This time the fountain solution is much more closely coupled to the actual surface energy of the non-imaging area. The fact that the dotted circle falls within the dashed circle indicates preferential wetting of the fountain solution over the surface in the presence of an inking roller. In other words, because the fountain solution lies within the dashed circle, the fountain solution will robustly reject ink in the non-imaging area. Note the arrangement of these curves and points is for illustrative purposes only and does not suggest that other configurations do not exist.

Unlike for traditional offset printing, all three spreading conditions must be satisfied over the single unique surface of the imaging member for variable lithographic printing. Such a solution has not been explored in the past due to the fact that traditional offset plates have two separate surfaces, so that the material and chemical properties of the ink, dampening fluid, and imaging surface were not so mathematically constrained. Thus, it is desirable for variable lithographic printing, where only a single imaging surface is used, to provide a dampening fluid wherein all three spreading conditions can be satisfied using only one surface (i.e. on one alpha-beta graph, not two) with a range of ink chemistries in order to provide robust printing quality.

The present disclosure contemplates a system where the dampening fluid is hydrophobic and the ink somewhat hydrophilic (having a small polar component). This system can be used with an imaging member surface which has low surface energy which is mainly dispersive in character. Thus it can work with an imaging member that is a silicone, fluorosilicone, or Viton® based elastomer, which offers high temperature wear robustness to the laser energy used in variable lithographic printing. An ink/dampening fluid/surface system of the present disclosure is representatively illustrated in FIG. 4. Here, the solid line circle represents the wetting conditions over a perfectly smooth surface. However, if a surface is micro-textured, the radius of the wetting condition of the surface can be effectively enlarged in the alpha beta space and the true wetting circle is represented by the dotted circle. This is due to the fact that the effective fractal surface area of the surface is increased, i.e. the factor r becomes larger than 1 and increases the effective wetting energy space allowable. This allows both the ink (represented by the triangle) and the dampening fluid (represented by the square) to fall within the textured wetting envelope of the surface. Therefore the surface energy of the surface (represented by the diamond) no longer falls directly on top of its own wetting envelope (the dotted circle). Note that the dampening fluid represented by the square is within the dashed circle formed by the surface energy of the plate (diamond) and the triangle (representing the ink) and this indicates that the surface is preferentially wetted by the fountain solution, even when ink is present.

When an energy source (such as a laser) is used to create a pattern in the dampening fluid layer, it is also desirable that the edges of the pattern remain stable over time. The surface texture which enhances the ink wetting also helps pin the dampening fluid in place to maintain the pattern. In addition, by using a dampening fluid surface tension that falls close to the smooth surface wetting curve, the spreading coefficient is minimized at the contact line (which does not see the effects of the microtexture roughness), thereby reducing the surface tension promoting spreading or pullback of the dampening fluid. Therefore by careful choice and design of the ink and dampening fluid chemistries and the re-imagable surface energy and texture, image quality can be improved both in terms of background tinting and image edge quality In such a system, the ink should have an appreciable polar surface tension and low dispersive surface tension. For example, ultraviolet (UV) offset inks based on acrylate oligomers and monomers have a recognizable polar surface tension component as well as having many other desirable characteristics. For example, UV-based lithographic printing has been used in packaging and sheetfed offset printing due to both environmental concerns and lower total cost of ownership. Smell issues that used to exist with such UV offset inks have generally been eliminated with the use of monomers having a higher boiling point. Indeed, some companies have an approved list that includes only UV offset inks, as other inks (e.g. cobalt cured or solvent-based inks) are sometimes considered to have greater risks in the packaging industry. The polar component of the surface tension of the UV offset ink can be tuned and controlled by choice of the proper monomer and oligomers for the ink, as well as by adding surface leveling agents to the ink. In other embodiments, the ink may comprise a monomer containing an ester (—COO—), ether (—O—), carbonyl (—CO—), amino (—NRR'), cyano (—CN), or hydroxyl (—OH) group. Exemplary monomers that can be used in a UV offset ink contemplated by the present disclosure include acrylates like methyl methacrylate or t-butyl acrylate; acrylonitriles, acrylamides, vinyl alcohol, etc.

By choosing the proper chemistry it is possible to devise a system where both the ink and the dampening fluid will wet the imaging member surface, but the ink and the dampening fluid will not mutually wet each other. The system can also be designed so that it is energetically favorable for dampening fluid in the presence of ink residue to actually lift the ink residue off of the imaging member surface by having a higher affinity for wetting the surface in the presence of the ink. In other words, the dampening fluid could remove microscopic background defects (e.g. <1 μm radius) from propagating in subsequent prints.

Generally speaking, the variable lithographic system can be described as comprising an ink, a dampening fluid, and an imaging member surface, wherein the dampening fluid has a surface energy alpha-beta coordinate which is within the circle connecting the alpha-beta coordinates for the surface energy of the ink and the surface energy of the imaging member surface. In particular embodiments, the dampening fluid has a total surface tension greater than 15 dynes/cm and less than 30 dynes/cm with a polar component of less than 5 dynes/cm. The imaging member surface may have a surface tension of less than 30 dynes/cm with a polar component of less than 2 dynes/cm. For example, the imaging member surface may be made of a silicone, fluorosilicone, or fluoroelastomer.

The dampening fluid of the present disclosure is useful for meeting all of the conditions listed above for digital variable lithographic printing. The dampening fluid comprises a solvent which is either a volatile hydrofluoroether (HFE) liquid or a volatile silicone liquid. The hydrofluoroether and silicone are liquids at room temperature, i.e. 25° C.

In specific embodiments, the volatile hydrofluoroether liquid has the structure of Formula (I):

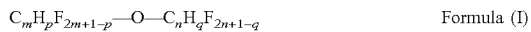

Formula (I)

wherein m and n are independently integers from 1 to about 9; and p and q are independently integers from 0 to 19. As can be seen, generally the two groups bound to the oxygen atom are fluoroalkyl groups.

In particular embodiments, q is zero and p is non-zero. In these embodiments, the right-hand side of the compound of Formula (I) becomes a perfluoroalkyl group. In other embodiments, q is zero and p has a value of 2m+1. In these embodiments, the right-hand side of the compound of Formula (I) is a perfluoroalkyl group and the left-hand side of the compound of Formula (I) is an alkyl group. In still other embodiments, both p and q are at least 1.

In this regard, the term "fluoroalkyl" as used herein refers to a radical which is composed entirely of carbon atoms and hydrogen atoms, in which one or more hydrogen atoms may be (i.e. are not necessarily) substituted with a fluorine atom, and which is fully saturated. The fluoroalkyl radical may be linear, branched, or cyclic.

The term "alkyl" as used herein refers to a radical which is composed entirely of carbon atoms and hydrogen atoms which is fully saturated and of the formula —$C_nH_{2n+1}$. The alkyl radical may be linear, branched, or cyclic. It should be noted that an alkyl group is a subset of fluoroalkyl groups.

The term "perfluoroalkyl" as used herein refers to a radical which is composed entirely of carbon atoms and fluorine atoms which is fully saturated and of the formula —$C_nF_{2n+1}$. The perfluoroalkyl radical may be linear, branched, or cyclic. It should be noted that a perfluoroalkyl group is a subset of fluoroalkyl groups, and cannot be considered an alkyl group.

In particular embodiments, the hydrofluoroether has the structure of any one of Formulas (I-a) through (I-h):

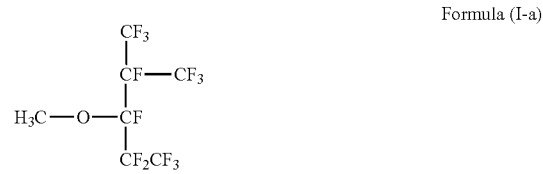

Formula (I-a)

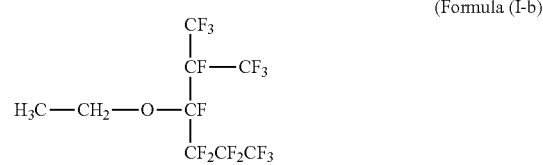

(Formula (I-b))

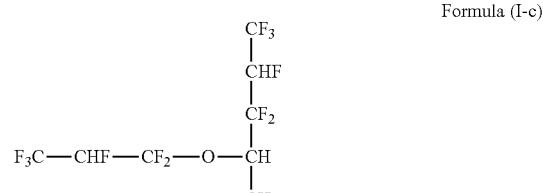

Formula (I-c)

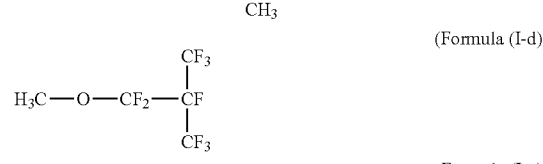

(Formula (I-d))

Formula (I-e)

(Formula (I-f))

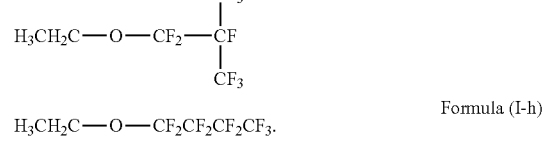

Formula (I-g)

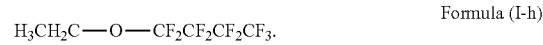

Formula (I-h)

Of these formulas, Formulas (I-a), (I-b), (I-d), (I-e), (I-f), (I-g), and (I-h) have one alkyl group and one perfluoroalkyl group, either branched or linear. In some terminology, they are also called segregated hydrofluoroethers. Formula (I-c) contains two fluoroalkyl groups and is not considered a segregated hydrofluoroether.

Formula (I-a) is also known as 1,1,1,2,2,3,4,5,5,5-decafluoro-3-methoxy-4-(trifluoromethyl)pentane and has CAS#132182-92-4. It is commercially available as Novec™ 7300.

Formula (I-b) is also known as 3-ethoxy-1,1,1,2,3,4,4,5,5,6,6,6-dodecafluoro-2-(trifluoromethyl)hexane and has CAS#297730-93-9. It is commercially available as Novec™ 7500.

Formula (I-c) is also known as 1,1,1,2,3,3-Hexafluoro-4-(1,1,2,3,3,3-hexafluoropropoxy)pentane and has CAS#870778-34-0. It is commercially available as Novec™ 7600.

Formula (I-d) is also known as methyl nonafluoroisobutyl ether and has CAS#163702-08-7. Formula (I-e) is also known as methyl nonafluorobutyl ether and has CAS#163702-07-6. A mixture of Formulas (I-d) and (I-e) is commercially available as Novec™ 7100. These two isomers are inseparable and have essentially identical properties.

Formula (I-f) is also known as 1-methoxyheptafluoropropane or methyl perfluoropropyl ether, and has CAS#375-03-1. It is commercially available as Novec™ 7000.

Formula (I-g) is also known as ethyl nonafluoroisobutyl ether and has CAS#163702-05-4. Formula (I-h) is also known as ethyl nonafluorobutyl ether and has CAS#163702-06-5. A mixture of Formulas (I-g) and (I-h) is commercially available as Novec™ 7200 or Novec™ 8200. These two isomers are inseparable and have essentially identical properties.

It is also possible that similar compounds having a cyclic aromatic backbone with perfluoroalkyl sidechains can be used. In particular, compounds of Formula (A) are contemplated:

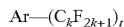  Formula (A)

wherein Ar is an aryl or heteroaryl group; k is an integer from 1 to about 9; and t indicates the number of perfluoroalkyl sidechains, t being from 1 to about 8.

The term "aryl" refers to an aromatic radical composed entirely of carbon atoms and hydrogen atoms. When aryl is described in connection with a numerical range of carbon atoms, it should not be construed as including substituted aromatic radicals. For example, the phrase "aryl containing from 6 to 10 carbon atoms" should be construed as referring to a phenyl group (6 carbon atoms) or a naphthyl group (10 carbon atoms) only, and should not be construed as including a methylphenyl group (7 carbon atoms).

The term "heteroaryl" refers to a cyclic radical composed of carbon atoms, hydrogen atoms, and a heteroatom within a ring of the radical, the cyclic radical being aromatic. The heteroatom may be nitrogen, sulfur, or oxygen. Exemplary heteroaryl groups include thienyl, pyridinyl, and quinolinyl. When heteroaryl is described in connection with a numerical range of carbon atoms, it should not be construed as including substituted heteroaromatic radicals. Note that heteroaryl groups are not a subset of aryl groups.

Hexafluoro-m-xylene (HFMX) and hexafluoro-p-xylene (HFPX) are specifically contemplated as being useful compounds of Formula (A) that can be used as low-cost dampening fluids. HFMX and HFPX are illustrated below as Formulas (A-a) and (A-b):

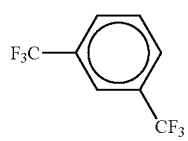  Formula (A-a)

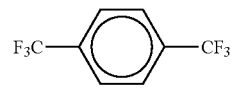  Formula (A-b)

It should be noted any co-solvent combination of fluorinated damping fluids can be assumed to help suppress non-desirable characteristics such as a low flammability temperature.

Alternatively, the dampening fluid solvent is a volatile silicone liquid. In some embodiments, the volatile silicone liquid is a linear siloxane having the structure of Formula (II):

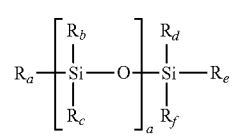  Formula (II)

wherein $R_a$, $R_b$, $R_c$, $R_d$, $R_e$, and $R_f$ are each independently hydrogen, alkyl, or perfluoroalkyl; and a is an integer from 1 to about 5. In some specific embodiments, $R_a$, $R_b$, $R_c$, $R_d$, $R_e$, and $R_f$ are all alkyl. In more specific embodiments, they are all alkyl of the same length (i.e. same number of carbon atoms).

Exemplary compounds of Formula (II) include hexamethyldisiloxane and octamethyltrisiloxane, which are illustrated below as Formulas (II-a) and (II-b):

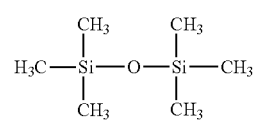  Formula (II-a)

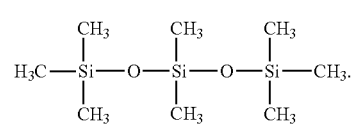  Formula (II-b)

In other embodiments, the volatile silicone liquid is a cyclosiloxane having the structure of Formula (III):

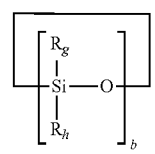  Formula (III)

wherein each $R_g$ and $R_h$ is independently hydrogen, alkyl, or perfluoroalkyl; and b is an integer from 3 to about 8. In some specific embodiments, all of the $R_g$ and $R_h$ groups are alkyl. In more specific embodiments, they are all alkyl of the same length (i.e. same number of carbon atoms).

Exemplary compounds of Formula (III) include octamethylcyclotetrasiloxane (aka D4) and decamethylcyclopentasiloxane (aka D5), which are illustrated below as Formulas (III-a) and (III-b):

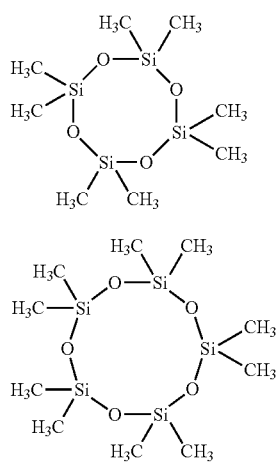

Formula (III-a)

Formula (III-b)

In other embodiments, the volatile silicone liquid is a branched siloxane having the structure of Formula (IV):

Formula (IV)

wherein $R_1$, $R_2$, $R_3$, and $R_4$ are independently alkyl or $-OSiR_1R_2R_3$.

An exemplary compound of Formula (IV) is methyl trimethicone, also known as methyltris(trimethylsiloxy)silane, which is commercially available as TMF-1.5 from Shin-Etsu, and shown below with the structure of Formula (IV-a):

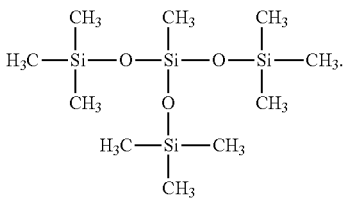

Formula (IV-a)

Any of the above described hydrofluoroethers/perfluorinated compounds are miscible with each other. Any of the above described silicones are also miscible with each other. This allows for the tuning of the dampening fluid for optimal print performance or other characteristics, such as boiling point or flammability temperature. Combinations of these hydrofluoroether and silicone liquids are specifically contemplated as being within the scope of the present disclosure. It should also be noted that the silicones of Formulas (II), (III), and (IV) are not considered to be polymers, but rather discrete compounds whose exact formula can be known.

In particular embodiments, it is contemplated that the dampening fluid comprises a mixture of octamethylcyclotetrasiloxane (D4) and decamethylcyclopentasiloxane (D5). Most silicones are derived from D4 and D5, which are produced by the hydrolysis of the chlorosilanes produced in the Rochow process. The ratio of D4 to D5 that is distilled from the hydrolysate reaction is generally about 85% D4 to 15% D5 by weight, and this combination is an azeotrope.

In particular embodiments, it is contemplated that the dampening fluid comprises a mixture of octamethylcyclotetrasiloxane (D4) and hexamethylcyclotrisiloxane (D3), the D3 being present in an amount of up to 30% by total weight of the D3 and the D4. The effect of this mixture is to lower the effective boiling point for a thin layer of dampening fluid.

The volatile hydrofluoroether liquids and volatile silicone liquids of the present disclosure have a low heat of vaporization, low surface tension, and good kinematic viscosity. For reference, Table 1 below compares their properties with that of water:

TABLE 1

| Compound | Heat of Vaporization at boiling point (kJ/kg) | Surface Tension at 25° C. (dynes/cm) | Kinematic Viscosity at 25° C. (cSt) | Vapor Pressure at 25° C. (mmHg) | Density (g/mL) | Solubility in Water (ppm) |
|---|---|---|---|---|---|---|
| Water | 2257 | 72 | 1 | 23.8 | 1 | — |
| (I-a) | 101.7 | 15 | 0.71 | 44.9 | 1.66 | 0.586 |
| (I-b) | 88.5 | 16.2 | 0.77 | — | 1.61 | <3 |
| (I-c) | 115.6 | 17.7 | 1.07 | — | 1.54 | <10 |
| (I-d)/(I-e) | — | 13.6 | — | 202 | 1.52 | 12 |
| (I-f) | 142 | 12.4 | 0.32 | 484.5 | 1.40 | 60 |
| (I-g)/(I-h) | 125.5 | 13.6 | — | 109 | 1.43 | <20 |
| (II-a) | 200.8 | 15.9 | 0.65 | 35 | 0.79 | — |
| (II-b) | 158 | 17.4 | 1 | 4 | 0.82 | — |
| (III-a) | 133 | 18.4 | 2.3 | 1.5 | 0.96 | — |
| (III-b) | 157 | 18.0 | 3.9 | 1 | 0.96 | — |
| (IV-a) | — | 16.8 | 1.5 | <10 | 0.85 | — |

An examination of Table 1 indicates that these liquid compounds all have much lower heats of vaporization, which reduces the amount of energy that needs to be provided at the imaging station to form the latent image. In addition, the liquid compounds have a much lower surface tension, such that surfactants may not need to be added at all. Many of the densities of these compounds also differ significantly from water, and they are generally insoluble with water as well.

In embodiments, the liquid solvent used in the dampening fluid has a heat of vaporization of less than 200 kJ/kg, or less than 120 kJ/kg when measured at 1 atmosphere and 25° C.

One result of using these liquids for the dampening fluid is that the dampening fluid can have a surface tension of from about 15 to about 30 dynes/cm. This low surface tension aids in spreading of the dampening fluid to wet the imaging member surface. In other particular embodiments, the dampening fluid has a kinematic viscosity of greater than 1 centiStokes at 25° C. and a surface tension of less than 72 dynes/cm at 25° C.

There are at least three conditions which desirably are met for a robust digital offset imaging system. First, the dampening fluid has a slight positive spreading coefficient so that the dampening fluid wets the imaging member surface. In addition, it is often still necessary that the dampening system used to coat the imaging surface member be as uniform and reproducible as possible. Initially, the dampening fluid spreads rapidly above the micro-roughness of the imaging member surface due to the positive spreading coefficient. This could be considered a "self-leveling" process which occurs passively and spontaneously. Secondly, the dampening fluid maintains a spreading coefficient in the presence of ink, or in other words the dampening fluid has a closer surface energy value to the imaging member surface than the ink does. This causes the imaging member surface to value wetting by the dampening fluid compared to the ink, and permits the dampening fluid to lift off any ink residue and reject ink from adhering to the surface where the laser has not removed dampening fluid. Third, the ink should wet the imaging member surface in air with a roughness enhancement factor (i.e. when no dampening fluid is present on the surface). It should be noted that the surface may have a roughness of less than 1 µm when the ink is applied at a thickness of 1 to 2 µm.

In addition to these three conditions, it is desirable that the dampening fluid should not wet the ink in the presence of air. In other words, fracture at the exit inking nip should occur where the ink and the dampening fluid interface, not within the dampening fluid itself. This way, dampening fluid will not tend to remain on the imaging member surface after ink has been transferred to a receiving substrate. In practice, this condition is difficult to achieve and small amounts of dampening fluid may need to be removed from the inking system by using an air knife to selectively evaporate away the dampening fluid from the inking system. Alternatively it may be acceptable to allow a small equilibrium build up of dampening fluid to emulsify within an inking subsystem.

Finally, it is also desirable that the ink and dampening fluid are chemically immiscible such that only emulsified mixtures can exist. Though the ink and the dampening fluid may have alpha-beta coordinates close together, often choosing the chemistry components with different levels of hydrogen bonding can reduce miscibility by increasing the difference in the Hanson solubility parameters.

Other additives may also be present in the dampening fluid. Such additives may include a biocide, a sequestrant, a corrosion inhibitor, and a humectant.

A biocide impedes the growth of or destroys any fungus or microorganisms that may be present in the dampening fluid. Exemplary biocides include sodium benzoate, phenol or derivatives thereof, formalin, imidazole derivatives, sodium dehydroacetate, 4-isothiazolin-3-one derivatives, benzotriazole derivatives, derivatives of amidine and guanidine, quaternary ammonium salts, derivatives of pyridine, quinoline and guanidine, derivatives of diazine and triazole, derivatives of oxazole and oxazine, bromonitropropanol, 1,1-dibromo-1-nitro-2-ethanol, and 3-bromo-3-nitropentane-2,4-diol. The biocide can be used in an amount of from about 0.001 wt % to about 1 wt % of the dampening fluid.

A sequestrant, or chelating agent, is used to chelate dissolved ions that may be present in the dampening fluid to prevent their reaction with other ingredients in for example the ink. Exemplary sequestrants include organic phosphonic acids and phosphonoalkanetricarboxylic acids, such as ethylenediaminetetraacetic acid (EDTA), diethylenetriaminepentaacetic acid, triethylenetetraminehexaacetic acid, hydroxyethylethylenediaminetriacetic acid, nitrilotriacetic acid, 1-hydroxyethane-1,1-diphosphonic acid, aminotri(methylenephosphonic acid), and salts thereof. The sequestrant can be used in an amount of from about 0.001 wt % to about 1 wt % of the dampening fluid.

A corrosion inhibitor protects the associated components of the imaging member from corrosion. Exemplary inhibitors include sodium nitrate, sodium phosphate, benzotriazole, 5-methylbenzotriazole, thiosalicylic acid, and benzimidazole.

A humectant prevents the dampening fluid from drying too rapidly, which can cause some problems with the final printed product. Exemplary humectants include ethylene glycol, glycerin and propylene glycol.

The dampening fluid of the present disclosure is based on a nonpolar solvent. It is contemplated that the dampening fluid would be used in a system in combination with an ink having a polar component.

Aspects of the present disclosure may be further understood by referring to the following examples. The examples are illustrative, and are not intended to be limiting embodiments thereof.

EXAMPLES

Figure 5:
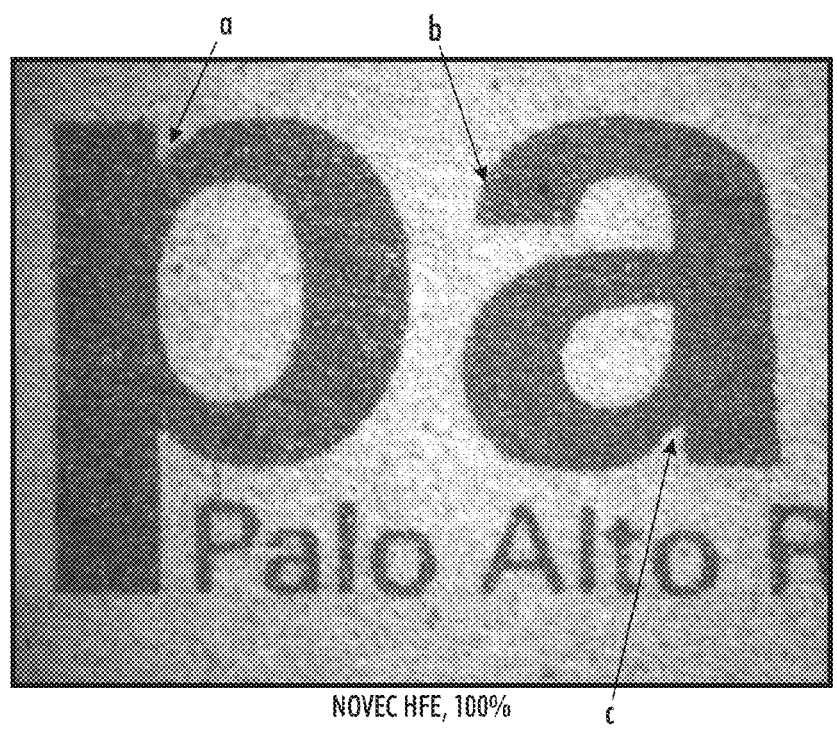
FIG. 5 is a view of a set of characters printed using a fountain solution of 100% Novec™ 7500.
Figure 6:
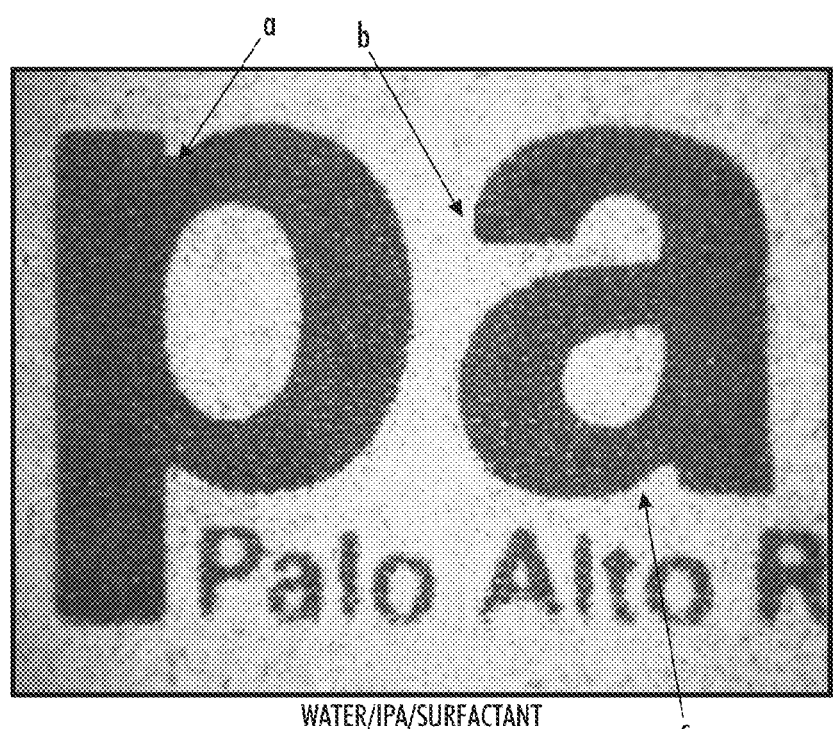
FIG. 6 is a view of the same set of characters printed using a water-based fountain solution for comparison with FIG. 5.

FIG. 5 is a view of a set of characters printed using a dampening fluid of 100% Novec™ 7500. FIG. 6 is a view of the same set of characters printed using a dampening fluid containing 90 wt % water, 8 wt % isopropanol, and 2 wt % SILSURF surfactant. Remember that the ink is laid down after the fountain solution. Comparing the arrows (a) in each Figure at the top of the "p", the corner is sharp in FIG. 5 and not rounded as in FIG. 6, indicating less pull back by the dampening fluid in FIG. 5. Similarly, comparing the arrows (b) in each Figure at the top left of the "a", the edges here are sharp in FIG. 5 and rounded in FIG. 6, again indicating less pull back by the dampening fluid in FIG. 5. The same effect is seen at the bottom right of the "a", which is marked with arrows (c).

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A process for variable digital lithographic printing, comprising:
applying a uniform layer of dampening fluid to a substantially smooth reimageable surface of an imaging member, the dampening fluid comprising a solvent which is a volatile silicone liquid;
forming a latent image by evaporating the dampening fluid from selective locations on the reimageable surface of the imaging member to form hydrophobic non-image areas and hydrophilic image areas, the volatility of the solvent promoting evaporation of the dampening fluid under comparatively lower levels of applied energy;
developing the latent image by applying a polar ink to the hydrophilic image areas formed on the reimageable surface; and
transferring the developed latent image from the reimageable surface to a receiving substrate,
wherein the solvent is a volatile silicone liquid having the structure of Formula (III)

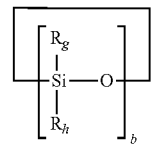

Formula (III)

wherein each $R_g$ and $R_h$ is independently hydrogen, alkyl, or perfluoroalkyl; and b is an integer from 3 to 8.

* * * * *